United States Patent [19]

Royer

[11] 4,349,530
[45] Sep. 14, 1982

[54] IMPLANTS, MICROBEADS, MICROCAPSULES, PREPARATION THEREOF AND METHOD OF ADMINISTERING A BIOLOGICALLY-ACTIVE SUBSTANCE TO AN ANIMAL

[75] Inventor: Garfield P. Royer, Worthington, Ohio

[73] Assignee: The Ohio State University, Columbus, Ohio

[21] Appl. No.: 215,426

[22] Filed: Dec. 11, 1980

[51] Int. Cl.³ .................... B01J 13/02; A61K 9/50
[52] U.S. Cl. ................................ 424/19; 424/22; 424/36; 424/316
[58] Field of Search .............. 424/19, 22, 36, 316

[56] References Cited

U.S. PATENT DOCUMENTS

| | | | |
|---|---|---|---|
| 3,137,631 | 6/1964 | Soloway | 128/264 |
| 3,202,731 | 8/1965 | Grevenstuk et al. | 264/7 |
| 3,429,827 | 2/1969 | Ruus | 252/316 |
| 3,558,507 | 1/1971 | Harbort | 252/316 |
| 3,565,818 | 2/1971 | Bayless | 252/316 |
| 3,639,259 | 2/1972 | Scarpelli | 424/36 X |
| 3,663,685 | 5/1972 | Evans | 424/1 |
| 3,796,669 | 3/1974 | Kiritani et al. | 252/316 |
| 3,937,668 | 2/1976 | Zolle | 252/316 |
| 4,147,767 | 4/1979 | Yapel | 424/22 |
| 4,169,804 | 10/1979 | Yapel, Jr. | 252/62.53 |
| 4,178,361 | 12/1979 | Cohen et al. | 424/22 |

FOREIGN PATENT DOCUMENTS

| | | |
|---|---|---|
| 505888 | 6/1979 | Australia . |
| 667 | 2/1979 | European Pat. Off. . |
| 2326934 | 5/1977 | France . |
| 795977 | 6/1958 | United Kingdom . |
| 1234805 | 6/1971 | United Kingdom . |
| 1516348 | 7/1978 | United Kingdom . |

OTHER PUBLICATIONS

Onica, D., et al., *Molecular Immunology,* 17, 783-789 (1980).
Lee, T., et al., *Science,* 213, 233 (1981).
Brandt, J., et al., *J. Peptide Protein Res.,* 8, 1976, 33-37.
Kolthoff, I., et al., *J. Am. Chem. Soc.,* 87(12), 2717-2720 (1965).
Onica, D., et al., *Immunochemistry,* 15, 941-944 (1978).

*Primary Examiner*—Richard A. Schwartz
*Attorney, Agent, or Firm*—Millard & Cox

[57] ABSTRACT

Implants, microbeads and microcapsules suitable for injection into an animal body comprise cross-linked but physically-native albumin and a non-albumin substance, for example a steroid or an enzyme. The microcapsules are formed under mild conditions (not above 37° C. and pH 4–10) from either a native albumin and a non-denaturing bi-functional cross-linking agent or a self-polymerizable albumin derivative. The method may be used to immobilize living cells such as yeast.

78 Claims, 4 Drawing Figures

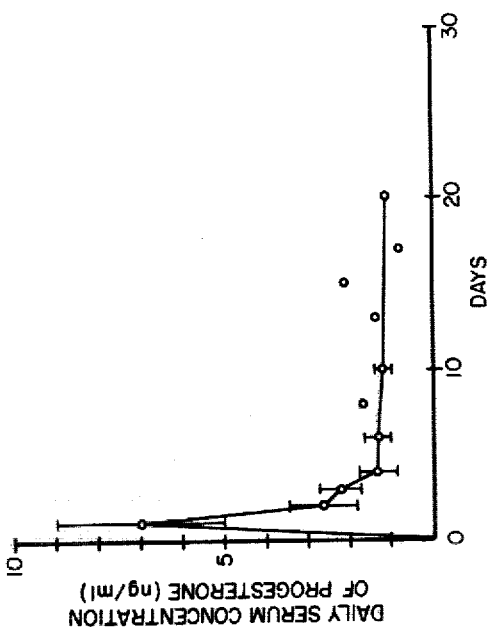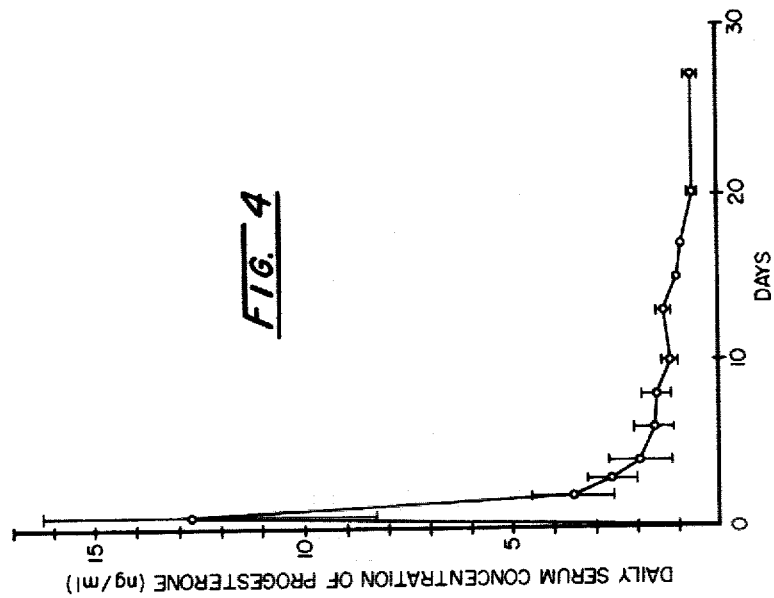

IMPLANTS, MICROBEADS, MICROCAPSULES, PREPARATION THEREOF AND METHOD OF ADMINISTERING A BIOLOGICALLY-ACTIVE SUBSTANCE TO AN ANIMAL

FIELD OF THE INVENTION

The invention relates to novel implants, microbeads and microcapsules, to a method for their preparation and to a method for administering a biologically-active substance to an animal using the novel microcapsules.

BACKGROUND OF THE INVENTION

A wide variety of substances have previously been formed into microcapsules and microbeads in order to improve their ease of handling and for other reasons. For example, it is known to microencapsulate small drops of dyes and to coat the microencapsulated dye onto one face of a backing sheet. The coated sheet then serves as a substitute for carbon paper, since the impact of a typing element of a typewriter upon the coated sheet ruptures the microcapsules and allows the dye to flow from the ruptures and mark the desired character upon an adjacent sheet of plain paper. The coated sheet has the advantage over normal carbon paper that mere finger pressure will not rupture the microcapsules and thus the sheet can be freely handled without risk of staining the fingers.

During microencapsulation, a small drop or crystal of an active substance, typically about 0.1 mm in diameter, is surrounded by a thin film of a capsule-forming carrier material. In contrast, a microbead comprises a solid, substantially spherical particle of the bead-forming carrier material with the active substance dispersed therethrough. The carrier material not only prevents the active material from running (if it is a liquid) but also isolates the active material from the external environment. For example, an easily oxidizable substance can be stored in microencapsulated form without undergoing oxidation by atmospheric oxygen. Many biologically-active materials are susceptible to chemical changes during storage and microencapsulation is one possible way of protecting such substances from chemical change during storage. Moreover, if a microencapsulated biologically-active material could be produced which was suitable for injection into an animal body the active material could be released slowly into the blood stream as the capsule-forming material dissolves, thereby achieving the same type of "controlled release" action with injectable preparations as is achieved with orally administered large capsules which gradually dissolve within the alimentary canal.

Unfortunately, most previously known microcapsules or microbeads cannot safely be injected into an animal body without producing anaphylactic shock. The coating carrier material of an injectable microcapsule or microbead is desirably one which will dissolve in the blood stream in order to allow the active material within the microcapsules or microbeads to be released and to prevent undissolved microcapsules or microbeads blocking blood and other vessels. This obviously rules out synthetic resins as carrier materials. It is known to produce microbeads and microcapsules from proteins such as albumin (either natural albumin or albumin derivatives such as albumin active esters and albumin active intermediates), and it might be thought that such microbeads and microcapsules would be suitable for injection, since of course, albumin in its native state can readily be metabolized in an animal's bloodstream. However, albumins are globular proteins having a complicated stereochemistry which depends upon subtle chemical interactions between various parts of the protein molecule. The natural stereochemical configuration of a globular albumin molecule is easily destroyed by heat, changes in pH or chemical reagents and once this natural stereochemical configuration has been changed, the albumin is no longer readily metabolized in an animal's bloodstream. In order to employ albumin as a carrier material in microbeads and microcapsules, it is necessary to effect some form of cross-linking between the albumin molecules and the previously known techniques for effecting such cross-linking of albumin (temperatures of 50° C. or higher, sudden changes in pH, or chemical cross-linking agents such as formaldehyde and glyoxal) cause physical denaturation of the albumin and changes in its stereochemical configuration, usually by formation of lysino-alanine bridges. The resultant physically denatured protein microcapsule or microbead is not immunologically-acceptable. Although microcapsules or microbeads made from polylactic acid can be injected, the preparation of polylactic acid microcapsules and microbeads presents great technical difficulties.

I have now discovered that, by cross-linking albumin under appropriate, mild conditions, microbeads and microcapsules can be produced which can safely be injected into an animal's blood stream. The preparation of such albumin microbeads and microcapsules is not technically difficult. Moreover, although the mild cross-linking technique of my invention is primarily useful for the formation of microbeads and microcapsules, it may also be employed to produce macroscopic masses of cross-linked albumin having non-albumin materials dispersed therethrough and these larger masses of cross-linked albumin may be useful as implants.

SUMMARY OF THE INVENTION

The albumin used in the implants, microcapsules and microbeads of the invention may be a native albumin or a self-polymerizable albumin derivative such as an albumin active ester or an albumin active intermediate. The implants, microcapsules and microbeads are formed by dispersing the non-albumin substance in a solution of an albumin and causing the albumin to be cross-linked at a temperature not in excess of about 37° C. and at a pH of about 4 to about 10. If a native albumin is used, it is necessary to add to the albumin solution a bi-functional cross-linking agent having the property of cross-linking, but not physically denaturing albumin when the solution is maintained at a temperature not in excess of about 37° C. and a pH in the range of about 4 to about 10. If, however, an albumin active ester or an albumin active intermediate is used, the active groups on the ester or intermediate enable the compound to self-polymerize and no external cross-linking agent is necessary. Following the addition of the substance which it is designed to incorporate into the implant, microcapsules or microbeads (and the cross-linking agent, if necessary), the albumin solution is maintained at a temperature not in excess of about 37° C. and at a pH in the range of about 4 to about 10 until at least one body of cross-linked but physically native albumin containing the non-albumin substance forms in the albumin solution.

There are three principle variations of my method, depending upon whether implants, microcapsules or microbeads are desired. If a quantity of the albumin solution is allowed to cross-link so as to form a single body of physically-native albumin containing the non-albumin substance incorporated therein, the resultant albumin body is usable as an implant in an animal's body. If it is desired to produce microcapsules, the non-albumin substance is added to the albumin solution dissolved in a solvent immiscible with the albumin solution and is maintained in the form of droplets dispursed in the albumin solution, usually by vigourous stirring. Under these conditions, there are formed microcapsules comprising a core of the solution of the non-albumin substance surrounded by a coat of cross-linked but physically-native albumin. If desired, after these microcapsules have been formed, they may be washed to remove at least part of the immiscible solvent from their cores. Finally, if it is desired to produce microbeads, after the non-albumin substance has been added to the albumin solution, the albumin solution is dispersed as droplets in a liquid immiscible therewith while maintaining the albumin solution at a temperature not in excess of about 37° C. and a pH in the range of about 4 to about 10. Again, the necessary dispersion of the albumin solution in the immiscible liquid can usually be effected by vigorous stirring. Under these conditions, the dispersed droplets of albumin solution form microbeads of cross-linked but physically-native albumin having the non-albumin substance dispersed therein.

The invention extends to a composition of matter comprising a cross-linked but physically-native albumin (which may be a native albumin, an albumin active ester or an albumin active intermediate) and a non-albumin substance held within the albumin. The invention also extends to a method of administering a biologically-active substance to an animal using the novel implants, microbeads and microcapsules of the invention.

DETAILED DESCRIPTION OF THE INVENTION

As previously mentioned, the albumin used in the instant implants, microcapsules and microbeads may be a native albumin, an albumin active ester or an albumin active intermediate. For example, the native albumin may be bovine serum albumin or rabbit serum albumin. Advantageously, the albumin is one native to the animal into which the microcapsules are to be injected or implanted.

A wide variety of substances may be incorporated in the instant implants, microcapsules and microbeads. However, because the implants, microcapsules and microbeads can be formed under very mild conditions, they are particularly suitable for biologically-active substances, especially those which are sensitive to heat or to large changes in pH and which thus cannot be microencapsulated or microbeaded by previously known methods. For example, the instant implants, microcapsules and microbeads may contain steroids such as progesterone or norgestrel or enzymes such as asparaginase and proteases. Moreover because the temperatures used in the preparation of the instant implants, microcapsules and microbeads are low enough not to harm living cells, such cells may be incorporated into the instant implants, microcapsules and microbeads and thus immobilized. As is well-known, such immobilized cells may be employed to carry out chemical reactions, for example by allowing a solution of a substrate to flow through a column of microbeads containing cells having an enzyme capable of acting upon the substrate. Yeast cells are especially suitable for incorporation into the instant implants, microcapsules and microbeads.

In the process of the invention, the temperature at which the albumin solution is maintained during and after the dispersion of the non-albumin substance therein desirably does not exceed 20° C. and is preferably in the range of 0° to 10° C., most preferably 0° to 5° C.; the optimum temperature in most cases appears to be about 4° C. The pH of the albumin solution is preferably maintained in the range of about 5.5 to about 8.5 and most preferably about 7. To ensure reasonably rapid formation of the implants, microcapsules or microbeads, the albumin solution should be relatively concentrated, being at least 10% w/v. However, it is preferred that the concentration of the albumin solution not exceed about 50% w/v and preferably not exceed 30% w/v. Although the albumin solution may be a purely aqueous solution, in some cases it is found advantageous to use an aqueous alcoholic solution of albumin.

When native albumin is being employed, appropriate bi-functional cross-linking agents include dithiobissuccinimidyl propionate, glutaraldehyde and ethylene glycolyl 6 (bissuccininidyl succinate), hereinafter referred to as EGS. A description of the preparation and properties of EGS is given in Abdella, P. M., Smith, P. K. and Rover, G. P., "A new cleavable reagent for cross-linking and reversible immobilization of proteins", Biochemical and Biophysical Research Communications, 87(3), 734-742 (1979).

As already mentioned, to produce microcapsules the non-albumin substance should be added to the albumin solution in a solvent immiscible with the albumin solution. For example, if the albumin is dissolved in aqueous methanol or ethanol, the non-albumin substance may be added in the form of a chloroform solution. On the other hand, to produce implants or microbeads, the non-albumin substance is preferably added to the albumin solution in the form of crystals. In some of the instant implants and microbeads, crystals of the non-albumin substance may be seen within the implant or microbeads under a microscope, whereas in other instant implants and microbeads no such crystals are visible. However, the presence or absence of microscopically visible crystals appears to have little or no effect on the release of the non-albumin substance from the implants or microbeads.

Obviously, the instant implants will be directly implanted surgically in an animal body, whereas the microcapsules and microbeads will normally be administered by injection. However, the microcapsules and microbeads may be administered by other methods such as orally or in the form of implants.

After injection or implantation into an animal body, the instant implants, microcapsules and microbeads release the non-albumin substance contained therein relatively slowly as the cross-linked albumin is slowly dissolved, mainly by protease present within the animal body. Especially in the case of the instant microcapsules and microbeads, this sustained release action is desirable in that it avoids the initial high levels of active material produced in the blood stream by injection of simple solutions of the active material and thus provides a much more consistent level of active material within the bloodstream. The sustained release action may also render it possible to increase the interval between injections and to reduce the total number of injections necessary. Furthermore, it is an important advantage of the instant implants, microcapsules and microbeads that the rate of release of active material therefrom may be controlled by incorporating thereinto an inactive form of a protease capable of dissolving albumin. This inactive form of a protease is preferable a zymogen of a protease, preferably an acyl derivative of serine protease such as trypsin or chymotrypsin. The inactive form of the protease is incorporated into the implants, microcapsules or microbeads by simply dispersing it in the albumin solution with the active substance. The inactive form of the protease has no effect upon the microcapsules and microbeads when they are stored dry (and thus does not effect their shelf life) but when the microbeads or microcapsules are injected into an animal's bloodstream, the inactive form of the protease is gradually converted into the active form (usually by simple hydrolysis) and the active form of the protease attacks the albumin present in the microcapsules or microbeads, thereby speeding up the release of the active substance therefrom. If a zymogen of a protease is used, it will be appreciated that the first portion of the zymogen to be hydrolyzed to its active form will thereafter rapidly hydrolyze the remaining zymogen, thereby securing rapid release of encapsulated material from the microcapsules or microbeads.

BRIEF DESCRIPTION OF THE DRAWINGS

FIGS. 3 and 4 show progesterone levels in rabbits after, respectively, subcutaneous and intramuscular administration of the steroid by the instant method.

EXAMPLE 1

This example illustrates the preparation of microcapsules containing a steroid.

Bovine serum albumin (50 mg.) was dissolved in 5 ml. of 40% methanol. Norgestrel (15 mg.) and 1.13 mg. of dithiobissuccinimidyl propionate (a bi-functional cross-linking agent which does not physically denature albumin) were dissolved in 1 ml. of chloroform. Both solutions were cooled to 4° C. and were near neutral pH. A chloroform solution was then slowly added to the albumin solution under vigorous stirring, thereby forming an emulsion of tiny chloroform droplets in the albumin solution. The size of these droplets is dependent on the speed of stirring; the higher the stirring speed, the smaller the droplets. The emulsion was maintained at 4° C. for three hours; at the end of this time, the droplets had formed into microcapsules. After one hour's further standing at room temperature the surface of the droplets "wrinkled" indicating the formation of an albumin membrane. The chloroform core of the microcapsules was then removed by washing with methanol, after which the microcapsules could be stained with coomassie blue, thus confirming that the skin of the microcapsules consisted of physically native albumin.

EXAMPLE 2

This example illustrates the preparation of microbeads containing steroids and their injection into rabbits.

Rabbit or bovine serum albumin (600 mg.) was dissolved in 2.4 ml. of 0.1% sodium dodecyl sulfate in 1 mM. sodium phosphate buffer, pH 7.5. The solution was cooled to 4° C. and 39 mg. of a finely divided steroid (progesterone or norgestrol) were dispersed in the solution, followed by 0.6 ml of a 5% v/v aqueous solution of glutaraldehyde. The resultant dispersion was quickly pipetted into 150 ml. of a vigorously stirred 1:4 mixture of corn oil and petroleum ether in a 250 ml. beaker. The stirring was continued for 15 minutes, at the end of which time solid microbeads had settled to the bottom of the beaker. The corn oil/petroleum ether mixture was decanted and the microbeads washed three times with petroleum ether and dried in a vacuum desiccator. The dried beads were then incubated twice with 25 ml. of 0.1% w/v serum albumin in 0.05 M Tris-Cl (tris(hydroxymethyl)aminomethane chloride) buffer, pH 8.6, for fifteen minutes. The microbeads were then washed with about 500 ml. of 1 mM. hydrochloric acid in a sintered glass filter funnel, the acid was washed off with distilled water and the beads were again dried in a vacuum desiccator.

Figure 1:
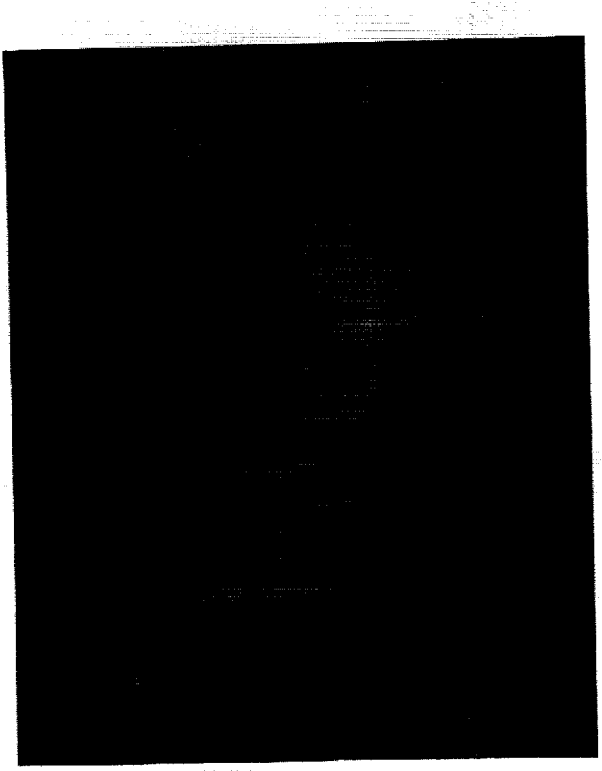
FIGS. 1 and 2 are views of two different types of microcapsules produced in the following examples.

The dried rabbit serum albumin/progesterone microbeads, which are illustrated in FIG. 1, were dark brown in color and 100–200 microns in diameter. Under 100× magnification, crystals of progesterone could be seen entrapped within the albumin. 70–250 mg. portions of the microbeads were suspended in corn oil and injected into rabbits weighing about 4 kg. Three rabbits received the injection subcutaneously, while three other rabbits received it intramuscularly. Progesterone in the serum was measured quantitatively by radioimmunoassay using the method of Powell, J. E. and Stevens, V. C., Clinical Chemistry 19(2), 210–215 (1973). The progesterone levels in the rabbits which had received the microbeads subcutaneously are shown in FIG. 3, while the progesterone levels in the rabbits which received the microbeads intramuscularly as shown in FIG. 4. It will be seen that in both cases significant progesterone levels were present in the rabbit's bloodstream for a period of 20 days after injection. Control animals received similar amounts of progesterone dispersed in corn oil but not encapsulated. In the control animals, progesterone levels in the bloodstream diminished to zero in less than two days.

The injections were repeated at intervals of one month. Six days after the third injection, one of the rabbits which had received the progesterone intramuscularly was sacrificed. The injection sites were examined and found to be devoid of inflammation or any other abnormal appearance. The microbeads had completely disappeared from the site of the third injection. The injections into the other rabbits were continued at monthly intervals for seven months. Throughout the experimental period no adverse allergic responses were observed in either rabbit and the body weight, temperature and general condition of the rabbits appeared normal. No inflammation or necrosis was observed at the injection sites even in the rabbit in which the injections were continued over seven months. In the rabbits receiving the injections subcutaneously, the microbeads disappeared completely although their disappearance was slower than in the case of the rabbits receiving the intramuscular injections.

A further test using similar capsules which had been kept at 140° C. for four hours (and in which the albumin was therefore denatured) showed a very much slower rate of release of progesterone. Moreover, these capsules heated to 140° C. are not degraded by proteases.

EXAMPLE 3

This example illustrates the formation and assay of bovine serum albumin/asparaginase microbeads.

Bovine serum albumin (400 mg.) was dissolved in 1.6 ml. of 0.1 M sodium phosphate buffer, pH 7.4, at 4° C. of asparaginase (15 mg.) was then dispersed in this albumin solution and then 0.4 ml. of a 5% v/v aqueous solution of glutaraldehyde was mixed quickly with the albumin solution. In the same manner as in Example 2, the mixed solution was then suspended in 150 ml. of a 1:4 corn oil/petroleum ether mixture with vigorous stirring. After fifteen minutes, microbeads had settled to the bottom of the beaker containing the oil phase, which was then decanted. The microbeads were washed three times with petroleum ether and dried in a vacuum desiccator.

Figure 2:
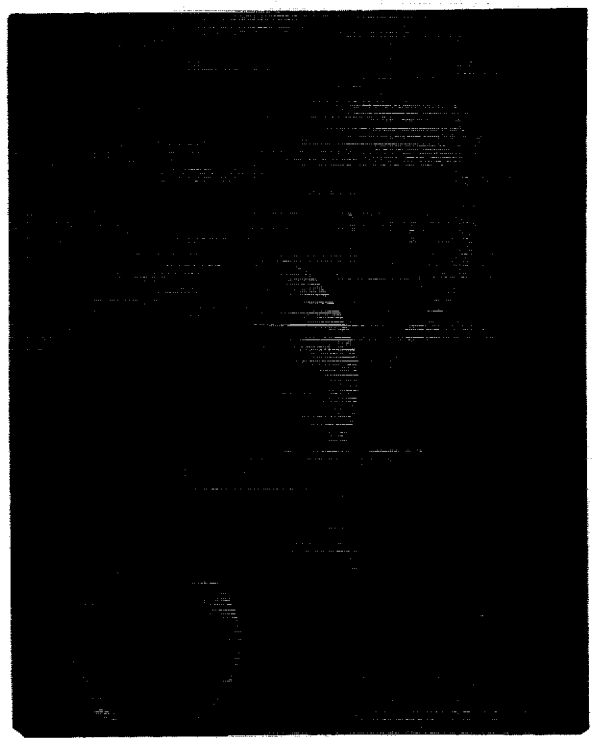

The resultant microbeads, which are illustrated in FIG. 2, displayed physical characteristics similar to the microbeads produced in Example 2, except that no crystals of the enzyme were visible within the albumin polymer.

The activity of the microencapsulated asparaginase was assayed. 7.6 Ml. of 0.01 M. asparagine in 0.05 M. Tris-Cl buffer, pH 8.6, and 0.4 ml. of the same buffer were mixed and brought to a temperature of 37° C. 20 Mg. of the asparaginase microbeads were added to the asparagine solution with stirring. After ten minutes, 0.1 ml. of the supernatant liquor was added to a mixture of 2 ml. of water and 0.2 ml. of Sigma Ammonia reagent (described in Winston, J. C., Jr., Methods in Enzymology (ed. Tabor, H. and Tabor, C. W.) XVII, 732, Academic Press, New York, 1970) to carry out Nessler's reaction. The mixture was then incubated at room temperature for 10 minutes and its absorbance at 480 nm was recorded, using an appropriate blank. The specific activity of the microbeaded asparaginase was 12.34 micromoles of asparagine hydrolyzed per minute per milligram of asparaginase, which is about 15.4% of the specific activity of native asparaginase.

EXAMPLE 4

This example illustrates the formation and assay of bovine serum albumin/yeast alcohol dehydrogenase microbeads.

Bovine serum albumin (600 mg) was dissolved in 2.4 ml. of 0.1 M. sodium phosphate buffer, pH, 7.4 at 4° C. The albumin solution was stirred vigorously and 9.6 mg. of yeast alcohol dehydrogenase, 54.21 mg. of nicotinamide adenine dinucleotide (NAD+) and 0.6 ml. of a 5% v/v aqueous solution of glutaraldehyde were quickly dispersed in the albumin solution. The mixed dispersion was then suspended in 150 ml. of the same oil mixture as in Examples 2 and 3. After 15-20 minutes, microbeads separated at the bottom of the oil mixture, which was then decanted. The microbeads were washed three times with petroleum ether and dried in a vacuum desiccator for several hours.

The dried microbeads were then suspended in 50 ml. of the same sodium phosphate buffer as before with stirring overnight at 4° C. At the end of this stirring, the microbeads were hydrated and swollen, while the supernatant buffer was cloudy, probably due to an oil/water emulsion formed by residual oil on the microbeads. The microbeads were then washed with distilled water in a sintered glass filter funnel and some were dried by lyophilization while others were dried in a vacuum desiccator.

The physical characteristics of the microbeads dried in the vacuum desiccator were similar to those produced in Examples 2 and 3, while the lyophilized microbeads had a fluffy appearance, but the alcohol dehydrogenase activity of the two preparations was substantially identical.

The microbeaded alcohol dehydrogenase was assayed in a 3 ml. cuvette in a Cary 15 spectrophotometer equipped with a microsubmersible magnetic stirrer. The production of NADH (the reduced form of NAD+) was followed by measuring the absorbance at 340 nm. The specific activity was determined as about 60 units per gram of microbeads.

It will be apparent to those skilled in the art that various changes may be made in the above-described implants microcapsules, microbeads and methods without departing from the scope of the invention herein involved. Accordingly, it is intended that all matter contained in the description thereof or shown in the accompanying drawings be interpreted as illustrative and not limitative, the scope of the invention being defined solely by the appended claims.

I claim:

1. A method of incorporating a non-albumin substance in a matrix of cross-linked but physically-native albumin, which method comprises:
    forming a solution of a native albumin;
    dispersing said substance and a bi-functional cross-linking agent in said albumin solution, said cross-linking agent having the property of cross-linking but not physically denaturing albumin when said solution is maintained at a temperature not in excess of about 37° C. and a pH in the range of about 4 to about 10, thereby forming a single phase containing both said albumin and said cross-linking agent; and
    thereafter maintaining said solution at a temperature not in excess of about 37° C. and at a pH in the range of about 4 to about 10 until at least one body of cross-linked but physically native albumin containing said substance forms in said solution.

2. A method according to claim 1 wherein said solution is allowed to form a single body of physically-native albumin containing said substance, said body being useable as an implant in an animal body.

3. A method according to claim 1 wherein said substance is added to said albumin solution dissolved in a solvent immiscible with said solution and said solution of said substance is maintained in the form of droplets dispersed in said albumin solution, thereby forming microcapsules comprising a core of said solution of said substance surrounded by a coat of cross-linked but physically-native albumin.

4. A method according to claim 3 wherein said formed microcapsules are thereafter washed to remove at least part of said immiscible solvent from their cores.

5. A method according to claim 1 wherein, after said substance and said cross-linking agent have been added to said albumin solutions, said albumin solution is dispersed as droplets in a liquid immiscible therewith while maintaining said solution at a temperature not in excess of about 37° C. and a pH in the range of about 4 to about 10, thereby forming microbeads of cross-linked but physically-native albumin having said substance dispersed therein.

6. A method according to claim 1 including maintaining said solution at a temperature in the range of about 0° to about 20° C. while said substance and said cross-linking agent are dispersed therein and thereafter until said body forms.

7. A method according to claim 6 including maintaining said solution at a temperature in the range of about 0° to about 10° C. while said substance and said cross-linking agent are dispersed therein and thereafter until said body forms.

8. A method according to claim 7 including maintaining said solution at a temperature in the range of about 0° to about 5° C. while said substance and said cross-linking agent are dispersed therein and thereafter until said body forms.

9. A method according to claim 1 including maintaining the pH of said solution within the range of about 5.5 to about 8.5 while said substance and said cross-linking agent are dispersed therein and thereafter until said body forms.

10. A method according to claim 9 including maintaining the pH of said solution at about 7 while said substance and said cross-linking agent are dispersed therein and thereafter until said body forms.

11. A method according to claim 1 wherein said bifunctional cross-linking agent is selected from the group consisting of dithiobissuccininidyl propionate, glutaraldehyde, and ethylene glycolyl bis (succinimidyl succinate).

12. A method according to claim 1 wherein the concentration of albumin in said solution, prior to dispersion of said substance and said cross-linking agent therein, is at least about 10% w/v.

13. A method according to claim 12 wherein the concentration of albumin in said solution, prior to dispersion of said substance and said cross-linking agent therein, is not more than about 50% w/v.

14. A method according to claim 13 wherein the concentration of albumin in said solution, prior to dispersion of said substance and said cross-linking agent therein, is not more than about 30% w/v.

15. A method according to claim 1 wherein said substance is an enzyme.

16. A method according to claim 1 wherein said substance comprises living cells.

17. A method according to claim 16 wherein said cells are yeast cells.

18. A method according to claim 1 including incorporating into said body an inactive form of a protease capable of dissolving albumin.

19. A method according to claim 1 including:
maintaining said albumin solution at a temperature in the range of about 0° to about 5° C. and a pH of about 7 while said substance and said cross-linking agent are dispersed therein and thereafter until said body forms; and
said substance being an enzyme.

20. A method according to claim 1 including dispersing said substance in said albumin solution in the form of solid crystals.

21. A method of incorporating a non-albumin substance in a matrix of cross-linked by physically-native albumin, which method comprises:
forming a solution of a self-polymerizable albumin derivative selected from the group consisting of albumin active esters and albumin active intermediates;
dispersing said substance in said albumin solution while maintaining said solution at a temperature not in excess of about 37° C. and a pH in the range of about 4 to about 10; and
thereafter keeping said solution at a temperature not in excess of about 37° C. and a pH in the range of about 4 to about 10 until at least one body of cross-linked but physically-native albumin containing said substance forms in said solution.

22. A method according to claim 21 wherein said solution is allowed to form a single body of physically-native albumin containing said substance, said body being useable as an implant in an animal body.

23. A method according to claim 21 wherein said substance is added to said albumin solution dissolved in a solvent immiscible with said solution and said albumin solution is thereafter stirred so as to maintain said solution of said substance in the form of droplets dispersed in said albumin solution, thereby forming microcapsules comprising a core of said solution of said substance surrounded by a coat of cross-linked but physically-native albumin.

24. A method according to claim 23 wherein said formed microcapsules are thereafter washed to remove at least part of said immiscible solvent from their cores.

25. A method according to claim 21 wherein, after said substance has been added to said albumin solution, said albumin solution is dispersed as droplets in a solution of a liquid immiscible therewith while maintaining said solution at a temperature not in excess of about 37° C. and at a pH in the range of about 4 to about 10, thereby forming microbeads of cross-linked but physically-native albumin having said substance dispersed therein.

26. A method according to claim 21 including maintaining said solution at a temperature in the range of about 0° to about 20° C. while said substance is dispersed therein and thereafter until said body forms.

27. A method according to claim 26 including maintaining said solution at a temperature in the range of about 0° to about 10° C. while said substance is dispersed therein and thereafter until said body forms.

28. A method according to claim 27 including maintaining said solution at a temperature in the range of about 0° to about 5° C. while said substance is dispersed therein and thereafter until said body forms.

29. A method according to claim 21 including maintaining the pH of said solution within the range of about 5.5 to about 8.5 while said substance is dispersed therein and thereafter until said body forms.

30. A method according to claim 29 including maintaining the pH of said solution at about 7 while said substance is dispersed therein and thereafter until said body forms.

31. A method according to claim 21 wherein the concentration of albumin in said solution, prior to dispersion of said substance therein, is at least about 10% w/v.

32. A method according to claim 31 wherein the concentration of albumin in said solution, prior to dispersion of said substance therein, is not more than about 50% w/v.

33. A method according to claim 32 wherein the concentration of albumin in said solution, prior to the dispersion of said substance therein, is not more than about 30% w/v.

34. A method according to claim 21 wherein said substance is an enzyme.

35. A method according to claim 21 wherein said substance comprises living cells.

36. A method according to claim 35 wherein said cells are yeast cells.

37. A method according to claim 21 including incorporating into the microcapsules a protease capable of dissolving albumin.

38. A method according to claim 21 including:
maintaining said albumin solution at a temperature in the range of about 0° to about 5° C. and a pH of about 7 while said substance is dispersed therein and thereafter until said body forms; and
said substance being an enzyme.

39. A method according to claim 21 including dispersing said substance in said albumin solution in the form of solid crystals.

40. A composition of matter comprising a cross-linked but physically-native albumin selected from the group consisting of cross-linked native albumins, cross-linked albumin active esters and cross-linked albumin active intermediates, and a non-albumin substance held within said albumin.

41. A composition according to claim 40 wherein said non-albumin substance is a biologically-active substance.

42. A composition according to claim 41 wherein said substance is a steroid.

43. A composition according to claim 41 wherein said substance is an enzyme.

44. A composition according to claim 41 wherein said substance comprises living cells.

45. A composition according to claim 44 wherein said cells are yeast cells.

46. A composition according to claim 40 in the form of an implant comprising a mass of cross-linked but physically-native albumin suitable for implantation in an animal body and having said non-albumin substance substantially uniformly dispersed therethrough.

47. A composition according to claim 40 in the form of a plurality of microcapsules, each of which comprises a core of said non-albumin substance surrounded by a coat of said albumin.

48. A composition according to claim 40 in the form of a plurality of microbeads, each of which comprises a mass of said albumin sufficiently small for injection into an animal body and having said non-albumin substance substantially uniformly dispersed therethrough.

49. A composition according to claim 40 further comprising an inactive form of a protease capable of dissolving albumin.

50. A composition according to claim 49 wherein said inactive form of a protease is an acyl derivative of a serine protease.

51. A method of administering a biologically-active substance to an animal, which method comprises implanting into said animal's body a composition according to claim 46.

52. A method of administering a biologically-active substance to an animal, which method comprises injecting into the animal body a composition according to claim 47 or 48.

53. A method of entraining a biologically-active substance in an albumin body and administering said body to an animal without inducing anaphylactic shock in said animal, which method comprises:
forming a solution of a native albumin,
dispersing said biologically-active substance and a bi-functional cross-linking agent in said albumin solution, said cross-linking agent having the property of cross linking but not physically denaturing albumin where said solution is maintained at a temperature not in excess of about 37° C. and a pH in the range of about 4 to about 10 thereby forming a single phase containing both said albumin and said cross-linking agent;
thereafter maintaining said solution at a temperature not in excess of about 37° C. and at a pH in the range of about 4 to about 10 until a body of cross-linked but physically native albumin containing said biologically-active substance forms in said solution;
separating said albumin body from any remaining solution; and
implanting at least part of said albumin body into said animal's body.

54. A method of entraining a biologically-active substance in an albumin body and administering said body to an animal without inducing anaphylactic shock in said animal, which method comprises:
forming a solution of a self-polymerizable albumin derivative selected from the group consisting of albumin active esters and albumin active intermediates;
dispersing said biologically-active substance in said albumin solution while maintaining said solution at a temperature not in excess of about 37° C. and a pH in the range of about 4 to about 10;
thereafter keeping said solution at a temperature not in excess of about 37° C. and a pH in the range of about 4 to about 10 until a body of cross-linked but physically-native albumin containing said biologically-active substance forms in said solution;
separating said albumin body from any remaining solution; and
implanting at least part of said albumin body into said animal's body.

55. A method of entraining a biologically-active substance in an albumin body and administering said body to an animal without inducing anaphylactic shock in said animal, which method comprises:
forming a solution of a native albumin;
dispersing in said albumin solution both a bi-functional cross-linking agent having the property of not denaturing albumin when said solution is maintained at a temperature not in excess of about 37° C. and a pH of about 4 to about 10 thereby forming a single phase containing both said albumin and said cross-linking agent, and a solution of said biologically-active material in a solvent immiscible with said albumin solution;
thereafter maintaining said albumin solution at a temperature not in excess of 37° C. and a pH in the range of about 4 to about 10 while maintaining said solution of said biologically-active substance in the form of droplets dispersed in said albumin solution, thereby forming microcapsules comprising a core of said solution of said biologically-active substance surrounded by a coat of cross-linked but physically-native albumin;
separating said microcapsules from said albumin solution; and
administering at least a portion of said separated microcapsules to said animal.

56. A method of entraining a biologically-active substance in an albumin body and administering said body to an animal without inducing anaphylactic shock in said animal, which method comprises:
forming a solution of a self-polymerizable albumin derivative selected from the group consisting of albumin active esters and albumin active intermediates;
dispersing in said albumin solution said biologically-active material in a solvent immiscible with said albumin solution while maintaining said albumin solution at a temperature not in excess of about 37° C. and at a pH in the range of about 4 to about 10;

thereafter maintaining said albumin solution at a temperature not in excess of about 37° C. and a pH in the range of about 4 to about 10 while maintaining said solution of said biologically-active substance in the form of droplets dispersed in said albumin solution, thereby forming microcapsules comprising a core of said solution of said biologically-active substance surrounded by a coat of cross-linked but physically-native albumin;

separating said microcapsules from said albumin solution; and administering at least a portion of said separated microcapsules to said animal.

57. A method according to claim 55 or 56 wherein said separated microcapsules are washed to remove at least part of said immiscible solvent from their cores before administration to said animal.

58. A method according to claim 55 or 56 wherein said microcapsules are administered to said animal by injection.

59. A method according to claim 55 or 56 wherein said substance is a steroid.

60. A method according to claim 55 or 56 wherein said substance is an enzyme.

61. A method according to claim 55 or 56 wherein said substance comprises living cells.

62. A method according to claim 61 wherein said cells are yeast cells.

63. A method according to claim 55 or 56 including incorporating into said microcapsules an inactive form of a protease capable of dissolving albumin.

64. A method according to claim 55 or 56 wherein said inactive form of a protease is an acyl derivative of a serine protease.

65. A method according to claim 55 or 56 including maintaining said albumin solution at a temperature in the range of about 0° to about 5° C. while said biologically-active substance is dispersed therein and thereafter until said microcapsules form.

66. A method according to claim 55 or 56 including maintaining the pH of said albumin solution within the range of about 5.5 to about 8.5 while said biologically-active substance is dispersed therein and thereafter until said microcapsules form.

67. A method of entraining a biologically-active substance in an albumin body and administering said body to an animal without inducing anaphylactic shock in said animal, which method comprises:

forming a solution of a native albumin;

dispersing in said albumin solution said biologically-active material and a bi-functional cross-linking agent having the property of not denaturing albumin when said solution is maintained at a temperature not in excess of about 37° C. and a pH in the range of about 4 to about 10 thereby forming a single phase containing both said albumin and said cross-linking agent;

dispersing said albumin solution as droplets in a liquid immiscible therewith while maintaining said solution at a temperature not in excess of about 37° C. and at a pH in the range of about 4 to about 10, thereby forming microbeads of cross-linked but physically-native albumin having said biologically-active substance dispersed therein;

separating said microbeads from said albumin solution; and administering at least a portion of said separated microbeads to said animal.

68. A method of entraining a biologically-active substance in an albumin body and administering said body to an animal without inducing anaphylactic shock in said animal, which method comprises:

forming a solution of a self-polymerizable albumin derivative selected from the group consisting of albumin active esters and albumin active intermediates;

dispersing in said albumin solution said biologically-active materials while maintaining said albumin solution at a temperature not in excess of about 37° C. and a pH in the range of about 4 to about 10;

dispersing said albumin solution as droplets in a liquid immiscible therewith while maintaining said solution at a temperature not in excess of about 37° C. and a pH in the range of about 4 to about 10, thereby forming microbeads of cross-linked but physically-native albumin having said biologically-active substance dispersed therein;

separating said microbeads from said albumin solution; and administering at least a portion of said separated microbeads to said animal.

69. A method according to claim 67 or 68 wherein said microcapsules are administered to said animal by injection.

70. A method according to claim 67 or 68 wherein said substance is a steroid.

71. A method according to claim 67 or 68 wherein said substance is an enzyme.

72. A method according to claim 67 or 68 wherein said substance comprises living cells.

73. A method according to claim 72 wherein said cells are yeast cells.

74. A method according to claim 67 or 68 including incorporating into said microcapsules an inactive form of a protease capable of dissolving albumin.

75. A method according to claim 74 wherein said inactive form of a protease is an acyl derivative of a serine protease.

76. A method according to claim 67 or 68 including maintaining said albumin solution at a temperature in the range 76. about 0° to about 20° C. while said substance is dispersed therein and thereafter until said microcapsules form; and said substance being an enzyme.

77. A method according to claim 67 or 68 including maintaining the pH of said albumin solution within the range of about 5.5 to about 8.5 while said substance is dispersed therein and thereafter until said microcapsules form; and said substance being an enzyme.

* * * * *